US006984621B1

(12) United States Patent
Sumi et al.

(10) Patent No.: US 6,984,621 B1
(45) Date of Patent: Jan. 10, 2006

(54) WOUND CONTRACTION INHIBITOR

(75) Inventors: Yukio Sumi, Nagoya (JP); Kenichiro Hata, Kariya (JP); Minoru Ueda, Nisshin (JP); Hisako Muramatsu, Nagoya (JP); Takashi Muramatsu, Nagoya (JP)

(73) Assignee: Japan Tissue Engineering Co., Ltd., Gamagori (JP)

( * ) Notice: Subject to any disclaimer, the term of this patent is extended or adjusted under 35 U.S.C. 154(b) by 351 days.

(21) Appl. No.: 10/111,620

(22) PCT Filed: Oct. 25, 2000

(86) PCT No.: PCT/JP00/07476

§ 371 (c)(1),
(2), (4) Date: Apr. 26, 2002

(87) PCT Pub. No.: WO01/30389

PCT Pub. Date: May 3, 2001

(30) Foreign Application Priority Data

Oct. 26, 1999 (JP) .................................. 11-304318

(51) Int. Cl.
A01N 37/18 (2006.01)
A61K 38/00 (2006.01)
A61K 31/70 (2006.01)
C07K 16/00 (2006.01)

(52) U.S. Cl. .............................. 514/2; 514/12; 530/324
(58) Field of Classification Search .................. 514/12, 514/2; 530/324
See application file for complete search history.

(56) References Cited

U.S. PATENT DOCUMENTS

| 5,376,633 | A | * | 12/1994 | Lezdey et al. | 514/8 |
| 5,532,215 | A | * | 7/1996 | Lezdey et al. | 514/8 |
| 5,633,227 | A | * | 5/1997 | Muller et al. | 514/12 |
| 5,780,440 | A | * | 7/1998 | Lezdey et al. | 514/21 |
| 5,871,956 | A | * | 2/1999 | Bandyopadhyay et al. | 435/69.1 |
| 6,017,880 | A | * | 1/2000 | Eisenberg et al. | 514/12 |
| 6,610,748 | B1 | * | 8/2003 | Yabuta et al. | 514/621 |

FOREIGN PATENT DOCUMENTS

| WO | WO 92/06706 A1 | 4/1992 |
| WO | WO 96/08275 A1 | 3/1996 |
| WO | WP 99/17800 A1 | 4/1999 |
| WO | WO 9943352 A1 * | 9/1999 |

OTHER PUBLICATIONS

Stetler et al., "Secretion of Active, Full- and Half-Length Human Secretory Leukocyte Protease Inhibitor by Saccharomyces cerevisiae," (1989) Bio/Technology, 7(1), 55-60.*

Eisenberg et al., "Location of the Protease-inhibitory Region of Secretory Leukocyte Protease Inhibitor" (May 15, 1990) The Journal of Biological Chemistry, 265(14), 7976-7981.*
McNeeley et al., "Secretory Leukocyte Protease Inhibitor: A Human Saliva Protein Exhibiting Anti-Human Immunodeficiency Virus 1 Activity In Vitro" (Jul. 1995) The Journal of Clinical Investigation, 96, 456-464.*
Thompson et al., "Isolation, Properties and Complete Amino Acid Sequence of Human Secretory Leukocyte Protease Inhibitor, A Potent Inhibitor or Leukocyte Elastase" (Sep. 15, 1986) Proc. Natl. Acad. Sci. USA, 83(18), 6692-6696.*
Lucey et al., "Recombinant Human Secretory Leukocyte-Protease Inhibitor: In Vitro Properties, and Amelioration of Human Neutrophil Elastase-Induced Emphysema and Secretory Cell Metaplasia in the Hamster" (1990) J. Lab. Clin. Med., 115(2), 224-232.*
Ohlsson et al., "Structure, Genomic Organization, and Tissue Distribution of Human Secretory Leukocyte-Protease Inhibitor (SLPI): A Potent Inhibitor of Neutrophil Elastase" (1986) Pulmonary Emphysema and Proteolysis, Academic Press, Inc., pp. 307-324.*
Sumi, Yukio et al., "Secretory Leukocyte Protease Inhibitor is a Novel Inhibitor of Fibroblast-medicated Collagen Gel Contraction," *Experimental Cell Research*, vol. 256, No. 1, Apr. 10, 2000, pp. 203-212.
Ashcroft, Gillian S. et al., "Secretory Leukocyte Protease Inhibitor Mediates Non-redundant Functions Necessary for Normal Wound Healing," *Nature Medicine*, vol. 6, No. 10, Oct. 2000, pp. 1147-1153.
Wingens, Miriam et al., "Induction of SLPI (ALP/HUSI-I) in Epidermal Keratinocytes," *The Journal of Investigative Dermatology*, vol. 111, No. 6, Dec. 1998, pp. 996-1002.

* cited by examiner

Primary Examiner—Christopher R. Tate
Assistant Examiner—Jennifer Harle
(74) Attorney, Agent, or Firm—Crompton, Seager & Tufte, LLC

(57) ABSTRACT

The pharmaceutical formulation for inhibiting wound contraction of the present invention includes secretory leukocyte protease inhibitor as an active ingredient. The SLPI concentration in the pharmaceutical formulation is preferably 1–5000 ng/ml, and more preferably 1–100 ng/ml. The pharmaceutical formulation for inhibiting wound contraction of the present invention may be prepared as an external preparation including a base and the SLPI as an active ingredient. The pharmaceutical formulation for inhibiting wound contraction of the present invention may be prepared as an injection including the SLPI as an active ingredient. The external preparation may preferably include a preservative. The injection may preferably include a stabilizer (an antioxidant), a preservative and an analgesic agent.

8 Claims, 2 Drawing Sheets

○ Comparative Example 1 (Normal Cell, Control)
□ Comparative Example 4 (Normal Cell, 10ng/mlTGF-β)
■ Example 5 (Normal Cell, 10ng/mlTGF-β+100ng/mlSLPI)

△ Comparative Example 5 (Hypertrophic Scar, Control)
▲ Example 6 (Hypertrophic Scar, 100ng/mlSLPI)

◇ Comparative Example 6 (Keloid, Control)
◆ Example 7 (Keloid, 100ng/mlSLPI)

SEQUENCE LISTING

<160> NUMBER OF SEQ ID NOS: 2

<210> SEQ ID NO 1
<211> LENGTH: 34
<212> TYPE: DNA
<213> ORGANISM: Artificial
<220> FEATURE:
<223> OTHER INFORMATION: synthetic oligonucleotide

<400> SEQUENCE: 1
caggtaccac caccatgaag tccagcggcc tctt                    34

<210> SEQ ID NO 2
<211> LENGTH: 29
<212> TYPE: DNA
<213> ORGANISM: synthetic oligonucleotide

<400> SEQUENCE: 2
atggtacctc aagctttcac aggggaaac                          29

WOUND CONTRACTION INHIBITOR

BACKGROUND OF THE INVENTION

The present invention relates to a wound contraction inhibitor for treating scar after the burn, hypertrophic scar, and keloid.

Skin tissues of such as the scar after a burn, the hypertrophic scar, and the keloid, lack cells and blood vessels, and are abundant with fibrous interstitial tissues, which are produced densely and irregularly, in the process for repairing the damaged tissues. Therefore, such damaged tissues are hard and have a light color. In addition, the damaged tissues tend to degrade their functionality and cause wound contraction.

It has been considered that these scars are caused by abnormal activity of the fibroblasts due to such things as infectious diseases, inflammations, and diathesis, and by resultant excessive production of collagen fibers in the process for the wound healing. However, the basic critical causes and mechanisms of the scars have not sufficiently been proved.

At present, either the surgical therapy after crisis (the secondary redressement) or the conservative treatment using medicine is mainly performed for these treatments. In the conservative treatment, tranilast, which is antiallergic drug, heparin ointment, steroids, and the like are used. These medicines suppress the infectious diseases and the inflammations, thereby inhibiting the wound contraction. Also, it has been observed that cytokine, such as interferon γ and interleukin-1, strongly inhibited wound contraction of the skin tissue in vitro. These are presently in the clinical trial.

However, in the conventional surgical therapy, there have been many cases in which recurrence happened and the complete recovery was not achieved. That is, not enough therapeutic effect was achieved. In addition, when the complete recovery was not achieved in the surgical therapy, it was required to simultaneously perform the mechanical oppression therapy or conservative therapy. Although the conventional conservative therapy showed the effect of inhibition as to the wound contraction of the skin tissues, there were many cases in which complete recovery was not achieved. That is, the conventional conservative therapy also does not achieve decisive results.

BRIEF SUMMARY OF THE INVENTION

The objective of the present invention is to solve the above problems of the prior art, and to provide a pharmaceutical formulation for inhibiting wound contraction that strongly inhibits the wound contraction.

The first aspect of the present invention is a pharmaceutical formulation for inhibiting wound contraction that includes secretory leukocyte protease inhibitor as an active ingredient.

Another aspect of the present invention includes a pharmaceutical formulation for inhibiting wound contraction that contains the secretory leukocyte protease inhibitor at a concentration of 1–5000 ng/ml.

The further aspect of the present invention includes a pharmaceutical formulation for inhibiting wound contraction that contains the secretory leukocyte protease inhibitor at a concentration of 1–100 ng/ml.

The further aspect of the present invention includes a pharmaceutical formulation for inhibiting wound contraction in which secretory leukocyte protease inhibitor is obtained by purifying the supernatant of cultured solution of oral mucosa epithelial cells.

In the further aspect of the present invention, the supernatant of the cultured solution of oral mucosa epithelial cells is made to adsorb using heparin affinity chromatography, and to elute the adsorbed fraction with a buffer containing 0.5 M sodium chloride. As a result of the elution, the resultant fraction is adsorbed using antihuman SLPI antibody immobilized immunoaffinity chromatography. Subsequently, the adsorbed fraction is eluted with 0.1 M glycine buffer to purify the secretory leukocyte protease inhibitor.

The pharmaceutical formulation for inhibiting wound contraction of the present invention may be prepared as an external preparation. It is preferable to prepare as an ointment. It is also preferable to include preservatives in the external preparation.

The pharmaceutical formulation for inhibiting wound contraction of the present invention may be prepared as an injection. It is preferable to include at least one of a stabilizer, a preservative and an analgesic agent in the injection.

DETAILED DESCRIPTION OF THE PREFERRED EMBODIMENTS

Figure 1:
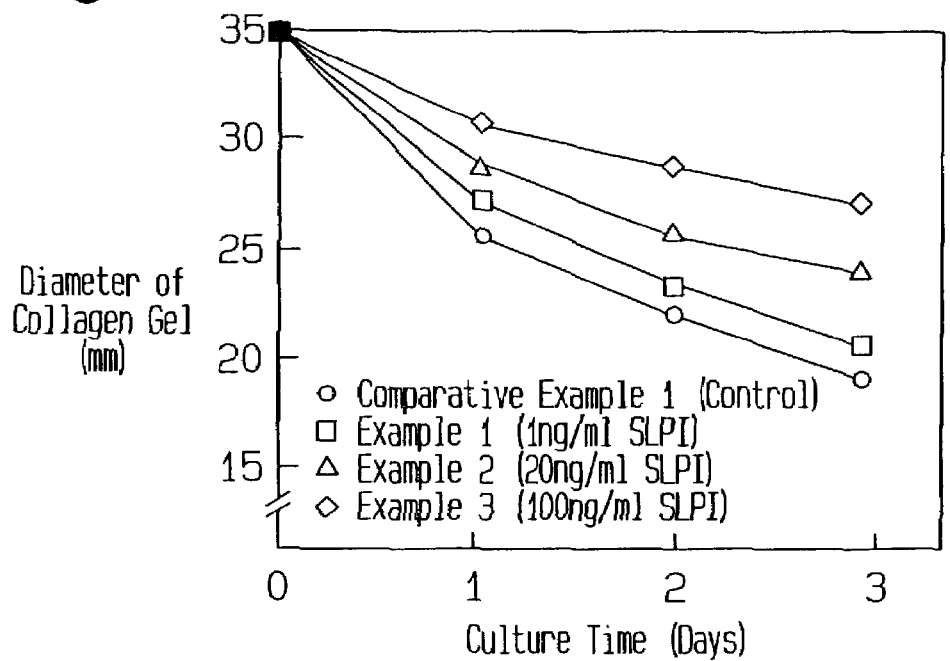
FIG. 1 illustrates a graph showing a result of in vitro gel contraction experiment 1.

The present invention will be described below in detail.

A pharmaceutical formulation for inhibiting wound contraction of the present invention includes secretory leukocyte protease inhibitor (hereafter referred as "SLPI") as an active ingredient. The SLPI is epithelial cell secreted protein, which is contained in such as skin, mucosa, blood, saliva, synovial fluid, and mucosa secretory of the human body, and is also serine protease inhibitor, which strongly inhibits the protease activity of human leukocyte elastase, cathepsin G, trypsin, and the like.

The SLPI has a molecular weight of approximately 12 kD (it may be recognized on the electrophoresis gel in the place of about 15 kD). The SLPI is a polypeptide consisting of 107 amino acids, has eight disulfide bonds in the molecule, and has a unique three-dimensional structure. In addition, the SLPI has signal sequence and no sugar chain in the N-terminal.

The SLPI may be purified, for example, from a supernatant of the cultured solution of oral mucosa epithelial cells. In this case, the supernatant of the cultured solution is adsorbed using heparin affinity chromatography, and then eluted with 0.5 M sodium chloride buffer. The resultant fraction may be adsorbed using the antihuman SLPI antibody immobilized immunoaffinity chromatography, and then may be purified by the elution with 0.1 M glycine buffer (pH 2.3).

The purified SLPI is preferably preserved in a buffer solution having a composition similar to the cultured solution of the oral mucosa epithelial cells or body fluid. More preferably, it is preserved in a 100 mM TRIS buffer (pH7.5) containing 10 mM calcium chloride and 0.1% human serum albumin since its composition is simple. In addition, it is preferable to refrigerate the purified SLPI under the light-shielded condition to prevent degeneration and oxidation of the SLPI protein. It is preferable to use the refrigerated SLPI within one month. It is more preferable to freeze the purified SLPI (e.g., at −30 to −20° C.). It is preferable to use the frozen SLPI within three months.

A concentration of SLPI in the pharmaceutical formulation is preferably 1–5000 ng/ml. The concentration of 1–100 ng/ml is more preferable since the substantial maximum effect of wound contracting inhibition is acquired at 100 ng/ml. When the concentration of SLPI is less than 1 ng/ml, sufficient wound contracting inhibition is not achieved. On the contrary, when the concentration of SLPI exceeds 5000 ng/ml, it is not economical since the SLPI is abundantly used.

The pharmaceutical formulation for inhibiting wound contraction of the present invention may be prepared as an external preparation. It is more preferable to prepare the pharmaceutical formulation as an ointment. The ointment may contain SLPI as an active ingredient and a base, and may be a homogeneous semisolid or paste form with an appropriate consistency. In addition, the ointment may preferably contain a preservative. The preservative is added to improve the stability of the ointment. The preservatives listed in Japanese pharmacopoeia are preferably used. The concentration of SLPI in the ointment may preferably be the same as the above pharmaceutical formulation for inhibiting the wound contraction.

Hydrophobic base, such as white petrolatum, petrolatum, Plastibase, silicones, white ointment, vegetable oil, lard, yellow bees wax, and white wax; hydrophilic base, such as macrogol; or non-fatty base, such as hydrogel, may be preferably used as a base.

The ointment is manufactured by the steps of preparing SLPI, base, and a preservative, as needed, and mixing them well to form a semisolid or paste. Here, it is necessary to avoid the heating to the utmost since the heating impairs the wound contracting inhibition of the SLPI protein. The ointment of the present invention may be preserved as the same procedure as the above pharmaceutical formulation for inhibiting wound contraction.

The external preparation is not limited to the ointment. It also may be prepared as pastes, cataplasma, liniments, lotions, or plasters in accordance with the Japanese pharmacopoeia. Further, it is preferable to apply the pharmaceutical formulation to sterilized cloth, paper, plastic film, or the like when it is used as the plaster. When it is affixed to the wound place, it is more preferable to use collagen film or chitin film, which promotes the healing.

The pharmaceutical formulation for inhibiting wound contraction may be a liquid injection containing SLPI as an active ingredient. The injection may preferably include at least one of a stabilizer (an antioxidant) for improving the stability of the injection, a preservative, and an analgesic agent that alleviates pain during the injection. Alternatively, the injection may include the combination of the stabilizer and the preservative, the combination of the stabilizer and the analgesic agent, or the combination of the preservative and the analgesic agent. Further, it is most preferable to include all of the stabilizer, the preservative, and the analgesic agent.

The stabilizers, the preservatives, and the analgesic agents listed in the Japanese pharmacopoeia are preferably used. In addition, the concentration of SLPI in the injection may preferably be the same as the above pharmaceutical formulation for inhibiting wound contraction. A solution for the injection may preferably be isotonic. In addition, the injection of the present invention may be preserved as the same procedure as the above pharmaceutical formulation for inhibiting wound contraction.

The above embodiments of the present invention have the following effects.

The pharmaceutical formulation for inhibiting wound contraction of the present invention, including the external preparation and the injection, contains SLPI as an active ingredient. Therefore, the wound contraction may be strongly inhibited. In addition, since the SLPI is a protein that exists everywhere in the human body, it is rare to cause side effects, thereby reducing the patient's burden during the treatment. It is also possible that the patient can endure administration at high doses and for a long period of time.

In the meantime, treatment for congenital tracheal cyst and treatment for fibroid lung that is caused due to the side effect of an anticancer drug are carried out using different activity of the SLPI. In these treatments, significant side effects after administrating the SLPI have not been reported at present. On the contrary, interferon γ and interleukin-1, which are considered to be effective for the treatment of the hypertrophic scar and the keloid, have reported side effects for treating the patient having diseases other than the hypertrophic scar and the keloid. Therefore, when these drugs are used for the treatment of the hypertrophic scar and the keloid, the possibility of causing side effects appears to be considerably high.

EXAMPLES

The present invention will now be described in more detail with reference to the following examples and comparative examples.

(Collection of Oral Mucosa Epithelial Cells and Preparation of the Culture System)

Human oral mucosa epithelial cells were obtained at Department of Dental and Oral Surgery, Nagoya University School of Medicine, with the consent of the patients. Here, donors are healthy adults and no abnormalities could be found in many screening tests against infectious diseases, hemograms and the like.

In the obtention, an area to be obtained was sufficiently sterilized with the 10% povidone-iodine solution, and then epithelial cells from the donor were obtained. The obtained epithelial cells were soaked in the culture medium for the transportation in the clean operation, and then preserved at 4° C. The culture system of obtained oral mucosa epithelial cells was made according to the methods of Rheinwald-Green (Nature, 265, 421–424 (1977)) and Hata et al. (Ann. Plast. Surg. 34, 530–538 (1995)).

The culture medium for the transportation contains 1000 U/ml penicillin G (manufactured by Meiji Seika Kaisha, Ltd.) 1 mg/ml streptomycin (manufactured by Sigma), 2.5 $\mu$g/ml amphotericin B (manufactured by Gibco) and 10% fetal calf serum (manufactured by Filtoron; hereafter referred as "FCS") in a Dulbecco's Modified Eagle's Medium (manufactured by Gibco; hereafter referred as "DMEM").

(Collection of Supernatant of Cultured Solution from Oral Mucosa Epithelial Cells)

When the oral mucosa epithelial cells cultured in the 10 cm Falcon dishes (made by Becton Dickinson Labware) reached confluent (approximately $2 \times 10^6$ cells/dish), the cells were sufficiently washed with the phosphate buffer solution. Subsequently, 10 ml DMEM cultured solution containing 10 $\mu$g/ml heparin (manufactured by Nakalai Tesque) was added to the cells, and the cells were cultured in an incubator (37° C., an atmosphere of 10% $CO_2$) for 48 hours. The supernatant obtained from the cultured solution was recovered, and passed through a 0.45 μm membrane filter. A filtrate was stored at 4° C., and used for experiments within 1 week.

(Preparation of the Human Fibroblast)

Regarding specimens of human normal skin, hypertrophic scar and keloid tissues, residual tissues after the operation were obtained at Departments of Dental and Oral Surgery and Plastic Surgery, Nagoya University School of Medicine, with the consent of patients. Here, the donors were found to have no abnormality in the infectious disease test and the blood test. Each of the tissues was cut off in 2 mm×2 mm square piece. Fibroblast of each tissue (i.e., normal skin tissue, hypertrophic scar tissue or keloid tissue) was obtained by explant culture from the piece.

More specifically, each piece was divided into 1 mm cube using scissors, three to five pieces of the cube were separately placed on the 35 mm plastic culture dish (made by Falcon Co.), and then DMEM cultured solution containing 10% FCS was added to the dish. Subsequently, tissues in each culture dish were cultured in an incubator (37° C., an atmosphere of 5% $CO_2$) for five to ten days. As a result, the fibroblasts emigrated from the periphery of the tissues, and adsorbed to the bottom surface of the culture dish while diffusing.

At the time when emigrated fibroblasts covered entire bottom surface of the culture dish, fibroblasts were separated and dispersed using a solution containing 0.05% trypsin (manufactured by Gibco) and 0.02% ethylenediaminetetraacetic acid (EDTA) to carry out the subculture. The subculture was repeated to obtain enough fibroblasts necessary for experiments. Here, the fibroblasts between 5th to 9th passages were used for the following experiments.

(Establishment of In Vitro Gel Contraction Experimental System)

In accordance with the method of Bell et al. (Pro. Natl. Acad. Sci., 76, 1274–1278 (1979)), in vitro gel contraction experimental system was established as follows. First, 2 ml of type I collagen acidic solution extracted from cattle corium (manufactured by Koken Co. Ltd.), 0.5 ml of FCS, and 0.5 ml of 6 fold concentrated Eagle minimum essential medium (manufactured by Nissui Pharmaceutical Co.) were mixed to produce 0.2% of collagen solution (pH 7.3). About $3\times10^5$ fibroblasts were suspended in the resultant collagen solution. The collagen solution was cultured in an incubator (37° C., an atmosphere of 5% $CO_2$) for five to ten minutes. After the viscosity of the collagen solution was increased and the collagen solution became the gel state, the solution was well mixed. Subsequently, the gel solution was dispensed into plastic culture dishes having 35 mm of diameter. Resultant collagen gel in the dishes was cultured in an incubator (37° C., an atmosphere of 5% $CO_2$) for 2 hours.

Then, the collagen gel was carefully washed in DMEM so that it may not be destroyed. Subsequently, the collagen gel was incubated in the DMEM cultured solution containing one of various test reagents (37° C., an atmosphere of 5% $CO_2$). The resultant gel was used for following in vitro gel contraction experiments. In the following experiments, collagen gel cultured in DMEM culture solution containing 10% FCS was used as control (a comparative example).

Regarding the measurement of the gel contraction, the diameter of the collagen gel was measured every 24 hours. Although the gel contraction was substantially uniformly generated, its shape is not circular. Therefore, the diameter of each gel was measured at three different places and the average diameter of these values was used.

(Purification and Identification of SLPI)

1) Heparin Affinity Chromatography

Protein component included in 3 liter of supernatant of the cultured solution of oral mucosa epithelial cells was applied to a heparin-Sepharose CL-6B column (made by Amersham Pharmacia Biotech Ltd.), and then successively eluted with 50 mM sodium phosphate buffer solution containing three different kind of salt concentrations (i.e., 0.5 M NaCl, 1.0 M NaCl, and 1.5 M NaCl) to collect the fraction.

Resultant fractions having different salt concentrations were used for in vitro gel experiments (the collagen gel including the normal fibroblasts). As a result, the contraction of the collagen gel using the fraction containing 0.5 M sodium chloride was remarkably inhibited in comparison with the fractions of control and the fractions containing the other concentrations of sodium chloride.

2) Immunoaffinity Chromatography 2 mg of antihuman SLPI antibody (manufactured by R&D systems Inc.) and 1 ml of CNBr-activated Sepharose CL-4 B (manufactured by Pharmacia Co.) were reacted in 100 mM sodium bicarbonate buffer solution containing 0.5 M sodium chloride (pH 8.8, 4° C.) for 12 hours. Next, antihuman SLPI antibody immobilized Sepharose was made by blocking remaining active groups with 1 M ethanolamine (pH 8.0). Subsequently, the excessive adsorbed protein was washed out with 100 mM sodium bicarbonate buffer containing 0.5 M sodium chloride (pH 8.0) and 100 mM sodium acetate buffer containing 0.5 M sodium chloride (pH 4.0). Next, the antibody immobilized Sepharose was filled with a column (diameter: 0.5 cm; length: 2.5 cm), and then washed with 50 mM sodium biphosphate buffer solution containing 0.2 M sodium chloride (pH 6.8) to equalize.

After the eluate containing 0.5 M sodium chloride, which was obtained by the heparin affinity chromatography, was adsorbed to the antihuman SLPI antibody immobilized Sepharose, it was eluted with 0.1 M glycine buffer (pH 2.3) to purify SLPI.

Resultant purified SLPI is used for in vitro gel experiments (collagen gel containing the normal fibroblasts). As a result, the contraction of the collagen gel was remarkably inhibited compared with the control eluted from the column without anti-human SLPI antibody. The quantative assay of the purified SLPI was carried out using SLPI ELISA (enzyme-linked immunosorbent assay) kit (made by R&D systems Inc.).

3) Polyacrylamide Gel Electrophoresis

Each fraction eluted from the heparin column was condensed by trichloroacetic acid precipitation and ethanol precipitation. Subsequently, the sample was developed on the gel using sodium dodecyl sulfate-polyacrylamide gel electrophoresis (SDS-PAGE). The protein retained on the gel was transferred onto a polyvinylidene fluoride (PVDF) membrane (Immobilon-PSQ made by Millipore), and stained with Coomassie brilliant blue.

As a result, the purified SLPI fraction had only included protein having a molecular weight of 15 kD. Although the other fractions had included contaminants other than the 15 kD protein, the stained amount of the 15 kD protein was substantially correspondent to the degree of the contraction inhibiting activity of the collagen gel.

4) N-Terminal Amino Acid Sequence

After excising the 15 kD protein from the PVDF membrane, amino acid sequence at the N-terminal of the protein was analyzed using ABI494A protein sequencer (made by Perkin-Elmer Japan Co., Ltd.). As a result, the deciphered amino acid sequence had 100% homology with a human SLPI.

5) Western Blotting Analysis

The PVDF membrane was analyzed with the antihuman SLPI antibody using Western blotting. As a result, only the band corresponding 15 kD protein was specifically colored.

6) The Confirmation of SLPI mRNA Expression

Total RNAs of the cultured oral mucosa epithelial cells were extracted using the guanidine isothiocyanate phenol chloroform method. Subsequently, first-strand cDNAs were synthesized from the total RNAs using the Superscript preamplification system (made by Gibco). Then, the cDNAs were amplified using the cDNA primer of SLPI by the polymerase chain reaction (PCR) method.

As a cDNA primer of the SLPI, the following primers, which added a restriction enzyme EcoRI site, 5' primer:

5'-CAGGTACCACCACCATGAAGTCCAGCG-GCCTCTT-3' SEQ ID NO. 1 and 3' primer:

5'-ATGGTACCTCAAGCTTTCACAGGGGAAAC-3' SEQ ID NO. 2 were made with reference to the study reported by ABE et al. (J. Clin. Invest., 87, 2207–2215 (1991)). Subsequently, 2 $\mu$l of the first strand cDNAs, 5 $\mu$l of 10×PCR buffer, and 0.5 $\mu$l of 12.5U/100 $\mu$l Taq polymerase (manufactured by Perkin-Elmer) were added to the primers, and then distilled water was added to bring the final volume to 50 $\mu$l. The resultant solution was used for the reaction.

The resultant reaction solution was carried out for PCR under the following condition. That is, after incubating the solution at 94° C. for 3 minutes, the degeneration process was performed at 94° C. for 30 seconds, the primer annealing process was performed at 55° C. for 30 seconds, and the elongation process was performed at 72° C. for 30 seconds. These three processes were recognized as one cycle. Totally, 35 cycles were carried out. The amplification products of the PCR were subjected to electrophoresis with 1.5% agarose gel, and stained with ethidium bromide. A single band was recognized.

Next, the single band (i.e., the amplification product of the PCR) was excised from the agarose gel in advance, cDNA was collected and purified using QIAEX II (made by QIAGEN). The cDNAs were subcloned into EcoRI site of plasmid vector pUC119.

The subcloned cDNAs were determined by the chain terminator method using an automated DNA sequencer (Li-Cor LC 4000 made by Li-Cor Co.). When a sequence that seems to be a normal sequence was compared with the base sequence of known human SLPI, both sequences were identical. Therefore, it was shown that cultured oral mucosa epithelial cells, which secrete contraction inhibiting active factor of collagen gel in the cultured solution, express mRNA of SLPI.

The above results 1) to 6) verified that human SLPI inhibits contraction of the collagen gel.

(In Vitro Gel Contraction Experiment 1)

SLPI purified by the immunoaffinity chromatography was added to the collagen gel containing normal fibroblasts, and then the contraction of the collagen gel was periodically observed. SLPI was added to the collagen gel so that the SLPI concentration in the collagen gel of examples 1, 2, and 3 was 1 ng/ml, 20 ng/ml, and 100 ng/ml, respectively. DMEM cultured solution containing 10% of FCS was used as a comparative example 1. The result was shown in Table 1.

The results regarding examples 1–3 showed that the contraction inhibiting activity of the collagen gel increases as the concentration of SLPI increases within the concentration range of 1–100 ng/ml. On the contrary, when in vitro gel contraction experiment was carried out using the sample in which 100 ng/ml of SLPI and antihuman SLPI antibody were simultaneously added, the contraction inhibiting activity of the collagen gel was degraded compared with example 3. Therefore, it was confirmed that the contraction inhibiting activity of the collagen gel was resulted from SLPI.

(In Vitro Gel Contraction Experiment 2)

Each of 100 ng/ml of purified SLPI (example 4), 100 U/ml of interleukin 1β (comparative example 2), and 1000 U/ml of interferon γ (comparative example 3) was added to the associated collagen gel containing normal fibroblasts, respectively. After three days, the diameter of each collagen gel was measured, and the contraction inhibiting rate (%) of each collagen gel was calculated. The results were shown in FIG. 2.

Figure 2:
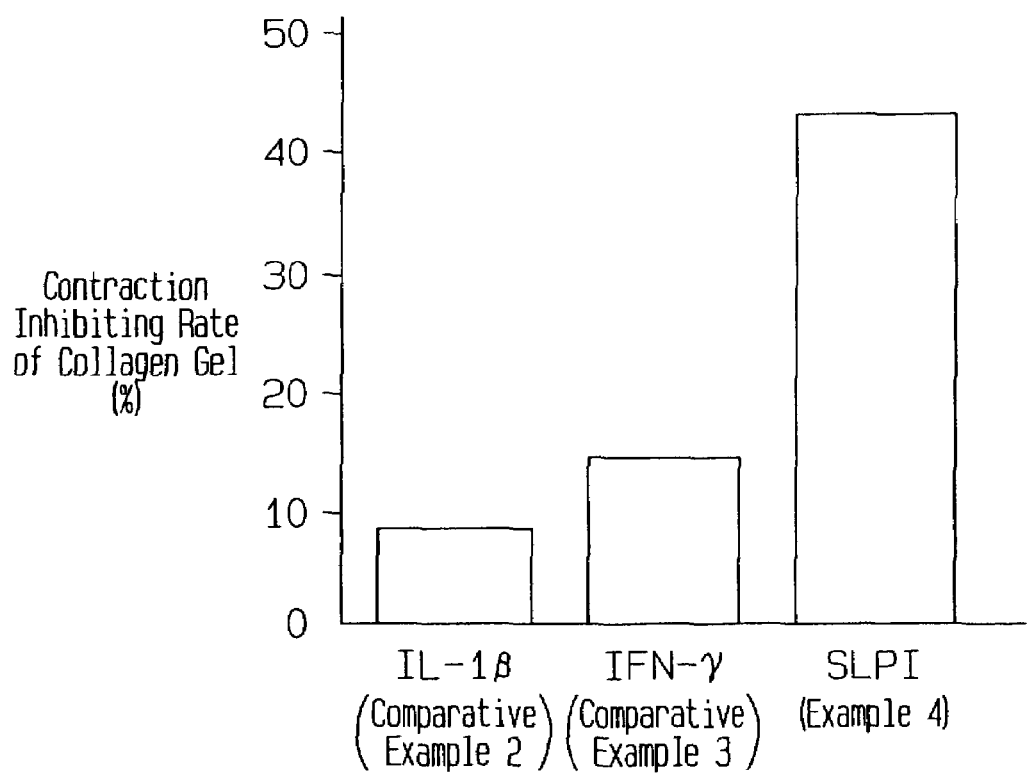
FIG. 2 illustrates a graph showing a result of in vitro gel contraction experiment 2.

As shown in FIG. 2, the contraction inhibiting activity of the collagen gel of example 4 (SLPI) was remarkably greater than that of interleukin 1β (comparative example 2) and interferon γ (comparative example 3).

(In Vitro Gel Contraction Experiment 3)

In vitro gel contraction experiment was carried out using collagen gel containing normal fibroblasts, collagen gel containing fibroblasts derived from a hypertrophic scar patient, and collagen gel containing fibroblasts derived from a keloid patient. During the experiment, the contraction of the collagen gel was periodically observed.

10 ng/ml of transforming growth factor (TGF-β) and 100 ng/ml of purified SLPI were added to the collagen gel containing normal fibroblasts (example 5). Also, DMEM cultured solution containing 10% of FCS (comparative example 1) or 10 ng/ml of TGF-β(comparative example 4) was added to the collagen gel containing normal fibroblasts, respectively.

100 ng/ml of purified SLPI (example 6), or DMEM cultured solution containing 10% of FCS (comparative example 5) was added to the collagen gel containing fibroblasts derived from a hypertrophic scar patient, respectively.

Figure 3:
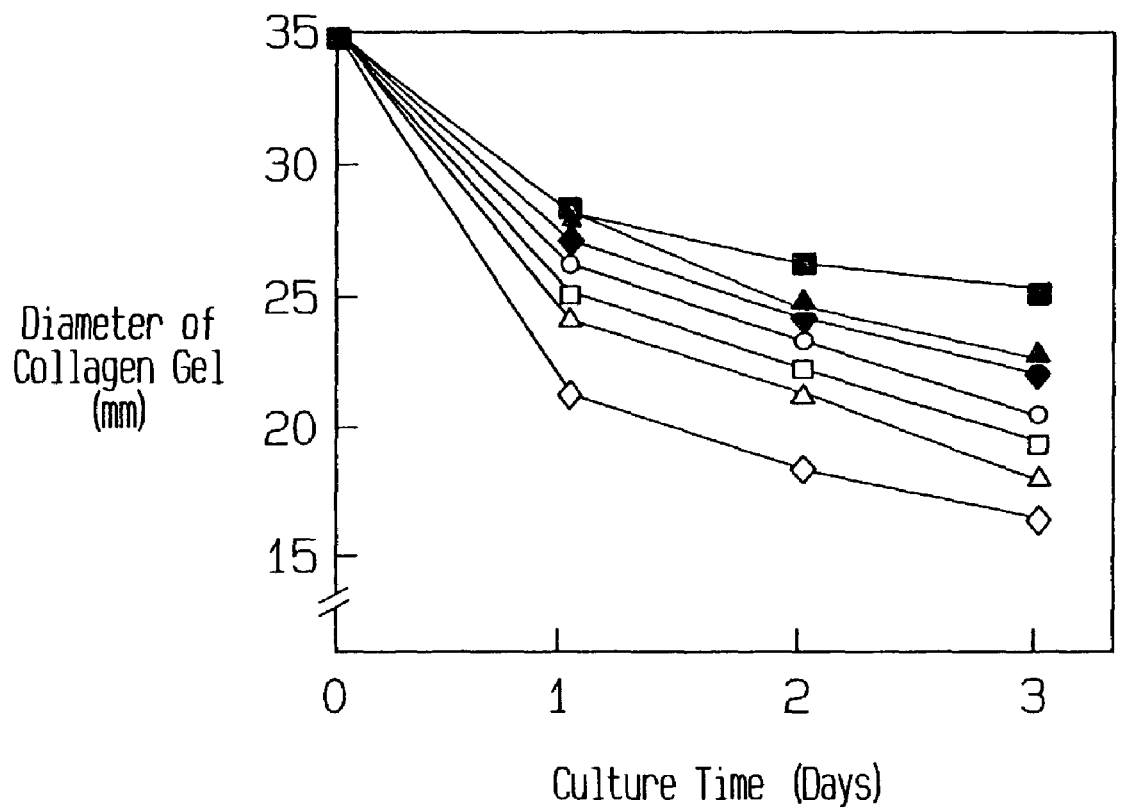
FIG. 3 illustrates a graph showing a result of in vitro gel contraction experiment 3.

100 ng/ml of purified SLPI (example 7), or DMEM cultured solution containing 10% of FCS (comparative example 6) was added to the collagen gel containing fibroblasts derived from a keloid patient, respectively. The results were shown in FIG. 3.

As a result, the collagen gel contraction inhibiting activity of each of examples 5–7 was greater than that of an associated comparative example, respectively. These results verified that SLPI displays the excellent therapeutic effect as wound contraction inhibitor for hypertrophic scar and keloid.

(Confirmation of Viable Cells)

Regarding comparative example 1 and example 3, the number of viable cells in the collagen gel during in vitro gel experiment 1 was periodically counted according to the method of Ehrlich et al. (Exp. Cell Res. 164, 154–162 (1986)). More specifically, cultured solution was removed from comparative example 1 or example 3 immediately after the in vitro gel experiment 1 was started, and every 24 hour, respectively. Subsequently, only the collagen gel was transferred to a 15 ml centrifuge tube (made by Falcon), and then DMEM containing 0.1% collagenase (manufactured by Wako Chemical) was added into the tube. These centrifuge tubes were shaken at 37° C. for 20 minutes, and lightly centrifuged to collect cell aggregation. Subsequently, the aggregation was resuspended in the DMEM, and the number of viable cells (cells/ml) was counted using a hemocytometer. The result was shown in Table 1.

TABLE 1

| Elapsed time | | Cell number (cells/ml) | | |
| --- | --- | --- | --- | --- |
| | Initial | After 24 hours | After 48 hours | After 72 hours |
| Com. Example 1 | $1.0 \times 10^5$ | $8.60 \pm 0.40 \times 10^4$ | $8.33 \pm 0.42 \times 10^4$ | $8.47 \pm 0.31 \times 10^4$ |
| Example 3 | $1.0 \times 10^5$ | $8.27 \pm 0.23 \times 10^4$ | $8.20 \pm 0.35 \times 10^4$ | $8.07 \pm 0.12 \times 10^4$ |

As shown in Table 1, the viable cells were confirmed in example 3 even when the fibroblast contacted SLPI, as in comparative example 1, in which no fibroblasts contacted SLPI. Accordingly, it was verified that the collagen gel contraction inhibiting activity by SLPI included in example 3 did not result from the stop of contraction due to the extinction of the fibroblasts.

(Confirmation and Consideration Regarding Effects of the Examples)

Basically, hypertrophic scar and keloid were specific diseases for human being. Therefore, it is very difficult to determine effects of the pharmaceutical formulation for inhibiting wound contraction in animal experiments. To correctly determine the effects of the wound contraction inhibitor, clinical trial must be required. However, it is remarkably difficult to evaluate quantitatively in the clinical trial. Therefore, an artificial dermis model, which is produced using human fibroblast and type I collagen that is a component included in skin, has been conventionally used for determining the effectiveness for these diseases.

The artificial dermis model forms the structure similar to a natural human dermis through gel contraction when nutrient components and fibroblasts are homogeneously mixed to type I collagen solution to produce gel. More specifically, the contraction process thereof is as follows. Immediately after the gel is produced, collagen fibers, which randomly contained in the gel, are rearranged due to the action of the fibroblasts. Subsequently, these fibers are crosslinked. This results in the gel contraction. The dermis-like structure is now clinically applied as an artificial skin in domestic and overseas.

The gel contraction of the artificial skin, which forms dermis-like structure, shows morphologically and pathologically very similar phenomenon as the wound contraction in human body. In addition, since increasing and decreasing of the number of cells is not substantially observed in the gel, the artificial skin reflects physiological phenomena of the skin tissue. Accordingly, it is possible to consider this contraction as wound contraction. In addition, it is also possible to consider factors that promote the gel contraction as wound healing promoting factor, and factors that inhibit the gel contraction as wound contraction inhibiting factor.

In fact, when tranilast or heparin, which is now clinically applied as the wound contraction inhibitor, or interferon, the effect of which is recognized in the clinical trial, is added to the artificial dermis model, the gel contraction is inhibited. Further, the fibroblast growth factor, which is now in the clinical trial as the wound healing promoter, is added to the artificial model, the promotion of the gel contraction is observed. Therefore, it is confirmed that the results using the artificial model are substantially identical with the clinical effects.

When the SLPI was added to the cultured solution of the gel contraction system and cultured them, significant inhibition for the gel contraction was observed. In addition, it was verified that this inhibiting effect is stronger than that of interleukin $1\beta$ and interferon $\gamma$, the effects of which are reported strongest at present. It was also confirmed by the following experiment that this effect was not resulted from the extinction of cells. That is, cells were isolated from the gel, the contraction of which was inhibited by the SLPI, and the isolated cells were cultured again while measuring the number of viable cells. As a result, it was confirmed that the number of viable cells was not changed, and all cells grew in the recultivation.

Also, the morphological observation of actin filament, tubulin, vinculin, integrin $\alpha 1$, $\alpha 2$ and $\beta 1$ of the fibroblasts in the gel were carried out using the fluorescent antibody staining. In the morphological observation, although the fibroblasts in the gel were alive, elongation interference of the cell projection was observed, and the formation of stress fiber by the actin filament was insufficient. However, it was observed that there gave no influence to the expression of the tubulin, which is a cytoskeleton component, and vinculin, which is a lining protein of the actin filament. Regarding the expression of integrin $\alpha 1$, $\alpha 2$, and $\beta 1$, there was no difference between the expression of integrin $\alpha 2$ and $\beta 1$. However, the expression of integrin $\alpha 1$, which increases in scar tissue and keloid, was inhibited. These results indicate that the actual fibroblasts in the hypertrophic scar or keloid tissues develop the abnormal cell projections as well as increase the number of cells, compared with the fibroblasts of the normal tissue. Also they show that SLPI inhibits the expression of the integrin $\alpha 1$ that is one of the causes of abnormal wound contraction in the scar tissues or keloid, and advantageously acts as wound contraction inhibitor.

Based on the above results, the same experiments were carried by using the fibroblasts obtained from the sites of hypertrophic scar and keloid. It was conventionally well known that the artificial dermis model using these cells showed stronger gel contraction than that using the normal cell. Therefore, the artificial dermis model using these cells was made and the gel contraction was observed. It was verified that the gel contraction was significantly promoted. However, when the SLPI was added to cultured solution of the artificial dermis model using these cells, the contraction was significantly inhibited. This result verified the effectiveness of the SLPI.

Considering from the above results, when an ointment and an injection containing the SLPI as an active ingredient is used for the treatment of hypertrophic scar or keloid, as is like the pharmaceutical formulation for inhibiting wound contraction of the above examples, the wound contraction of the wound site is considered to be strongly inhibited.

The present embodiments may be embodied with following modifications.

The epithelial cells of patients with scar after the burn, hypertrophic scar, or keloid are obtained and then cultured. SLPI is purified from the supernatant of the cultured solution to prepare the wound contraction inhibitor. The obtained wound contraction inhibitor may be used for the patient from whom the epithelial cells are collected.

In this case, allergic reaction and inflammatory reaction against the pharmaceutical formulation is surely suppressed.

What is claimed is:

1. A pharmaceutical formulation for inhibiting keloid and scar, the formulation comprising:
   1–100 ng/ml of a secretory leukocyte protease inhibitor as an active ingredient.

2. The pharmaceutical formulation for inhibiting keloid and scar according to claim 1, including said secretory leukocyte protease inhibitor at a concentration of 100 ng/ml.

3. The pharmaceutical formulation for inhibiting keloid and scar according to claim 1, wherein said secretory leukocyte protease inhibitor is obtained by purifying the supernatant of cultured solution of oral mucosa epithelial cells.

4. The pharmaceutical formulation for inhibiting keloid and scar according to claim 1, wherein said pharmaceutical formulation is prepared as an external preparation including a base and the secretory leukocyte protease inhibitor.

5. The pharmaceutical formulation for inhibiting keloid and scar according to claim 4, further comprising a hydrophobic base and a preservative, wherein said external preparation is prepared as an external ointment.

6. The pharmaceutical formulation for inhibiting keloid and scar according to claim 1, prepared as an injection including said secretory leukocyte protease inhibitor as an active ingredient.

7. The pharmaceutical formulation for inhibiting keloid and scar according to claim 6, including any one of a stabilizer, a preservative and an analgesic agent.

8. The pharmaceutical formulation for inhibiting keloid and scar according to claim 1, wherein said scar is a hypertrophic scar.

* * * * *